US00PP25893P3

(12) United States Plant Patent
Infante

(10) Patent No.: US PP25,893 P3
(45) Date of Patent: Sep. 15, 2015

(54) NECTARINE TREE NAMED 'ANDES NEC-3'

(50) Latin Name: *Prunus persica*
Varietal Denomination: Andes Nec-3

(71) Applicant: VIVEROS ASOCIADOS CHILE LTDA. (ANA Chile-Andes Nursery Association), Paine (CL)

(72) Inventor: Rodrigo Infante, Paine (CL)

(73) Assignee: Viveros Asociados Chile Ltda. (ANA Chile-Andes Nursery Association), Paine (CL)

( * ) Notice: Subject to any disclaimer, the term of this patent is extended or adjusted under 35 U.S.C. 154(b) by 168 days.

(21) Appl. No.: 13/766,215

(22) Filed: Feb. 13, 2013

(65) Prior Publication Data

US 2014/0230109 P1 Aug. 14, 2014

(51) Int. Cl.
*A01H 5/08* (2006.01)

(52) U.S. Cl.
USPC ..... Plt./190
CPC ..... *A01H 5/0856* (2013.01)

(58) Field of Classification Search
USPC ..... Plt./190
CPC ..... A01H 5/0856; A01H 5/0837
See application file for complete search history.

(56) References Cited

PUBLICATIONS

Rodrigo Infante et al., "'Andes-1': An Early-maturing Clingstone Peach Cultivar for Canning and Fresh Market", HortScience, vol. 46, No. 3, 2011, pp. 499-500.

*Primary Examiner* — Kent L Bell
(74) *Attorney, Agent, or Firm* — Greer, Burns & Crain Ltd.

(57) ABSTRACT

A new and distinct variety of clingstone nectarine tree denominated 'Andes Nec-3' which has fruit that is similar to 'Flavortop' nectarine that are yellow in flesh color, firm in texture, and balanced acid/sweet flavor. The variety is distinguished from the 'Flavortop' by having a more extended red blush, better taste, and longer postharvest life potential, and by producing fruit that is clingstone instead of freestone. The variety's harvest period is 10-12 days before the 'August Red' variety. Its fruit is solid red to purplish red blush, with a round, symmetrical fruit shape.

3 Drawing Sheets

Species: *Prunus persica* (Nectarine).
Cultivar name: 'ANDES NEC-3'.

This new cultivar resulted from controlled hybridization between the nectarine 'Flavor Top' (♀) and the nectarine genotype 'A67-03' (♂) performed in 1999 at Paine, Metropolitan Region, Chile (latitude –33°80'S, longitude –70°66'S, altitude 508 m above level. This tree was first asexually propagated on July 2004, and tested on a block of 20 cloned trees in the same experimental station at Paine. The new variety differs of his female progenitor 'Flavor Top', due it reaches higher content of soluble solids, reaching up to 13.5 whereas 'Flavor Top' seldom reaches more than 10.5-11.0; also because the blush of 'Andes Nec-3' covers 90-98% of its surface, while 'Flavor Top' seldom covers more than 60%. 'Flavor Top' in postharvest lasts no more than 14-21 days in good conditions, whereas 'Andes Nec-3' can maintain quality after 50 days in cold storage. On regard of its male progenitor, the selection 'A67-03' is less productive than 'Andes Nec-3', however even if it has a similar postharvest performance, it has high acidity, whereas 'Andes Nec-3' is a balanced sweet/acid cultivar, reaching ratios around 10 to 12.

Distinctive characteristics of the variety: Semi upright plant growth, medium vigor. Fruit round, symmetrical, solid 90 to 98% red blush. Harvest period 10-12 days before 'August Red'.

This cultivar main feature is a slow pulp softening rate during the last two weeks before the commercial harvest. This feature enables delaying harvesting, pursuing the increase of the fruit size and soluble solids content without affecting their postharvest life potential. Secondly it shows a high postharvest life potential, which can reach up to 50 days at 0° C. while maintaining its initial sensory quality. From a sensory point of view this is a variety of medium to high acidity with a balanced sweetness/acidity ratio and in general an average overall sensory quality. The variety is not susceptible to "chilling injury" and therefore can be used for exporting to distant markets.

BRIEF DESCRIPTION OF THE FIGURES

The Drawings of the nectarine of the present variety are color photographs.

Figure 1:
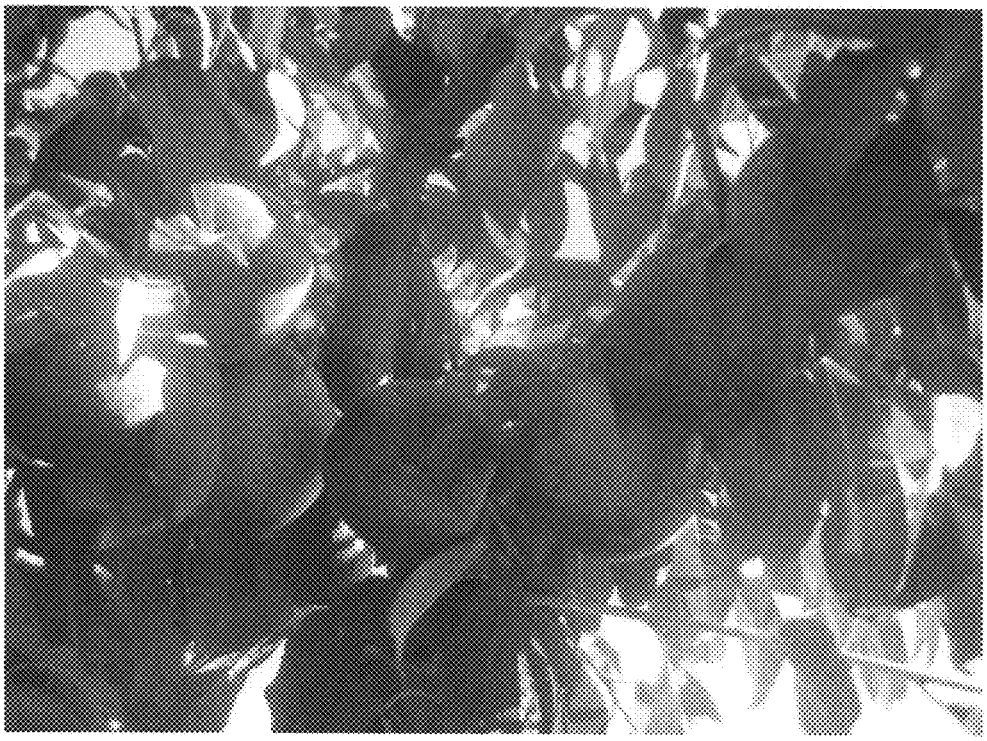
FIG. 1 shows typical specimens of the whole fruit in skin color and form, on tree, and typical leaves.
Figure 2:
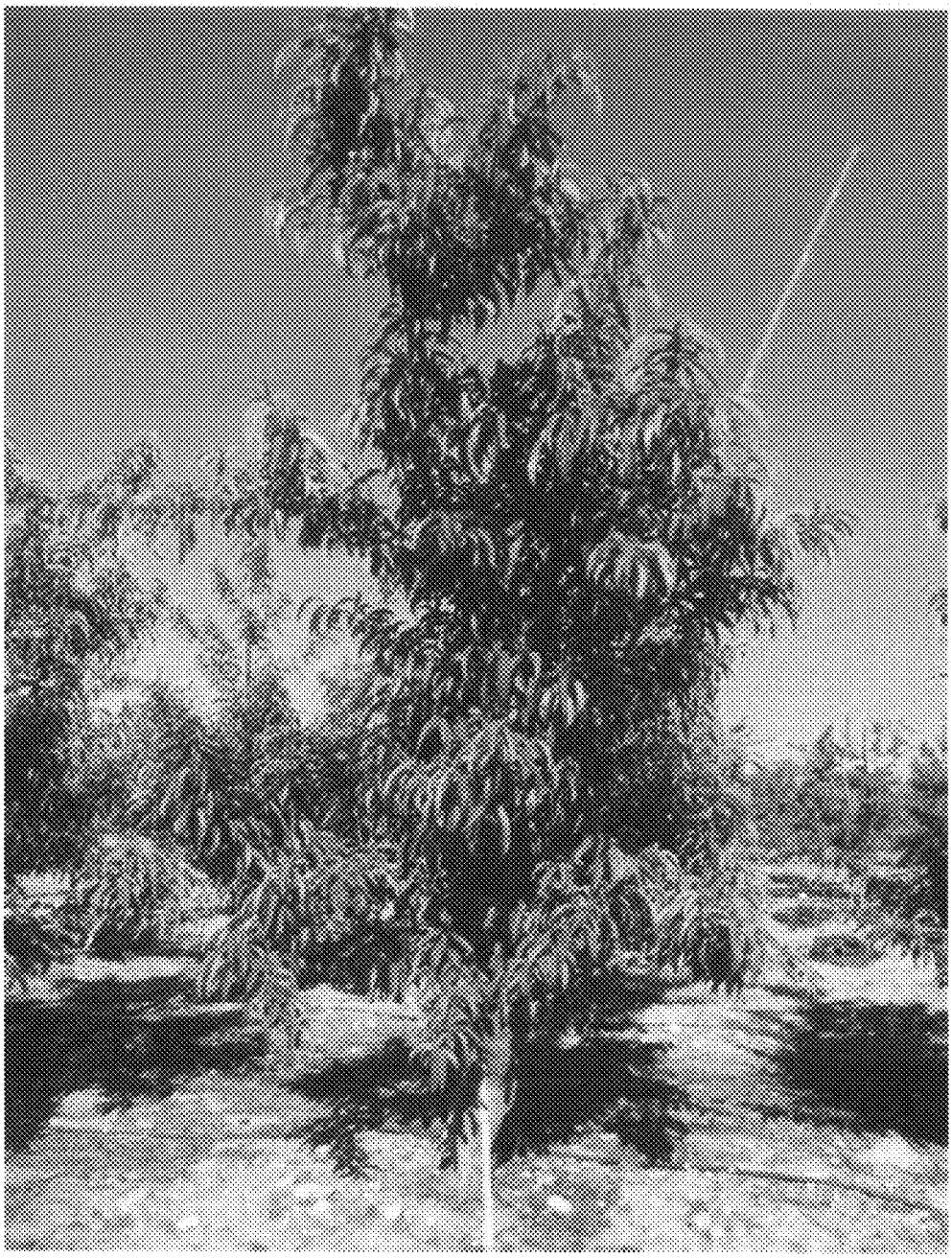
FIG. 2 shows a the tree of 'Andes Nec-3'.
Figure 3A:
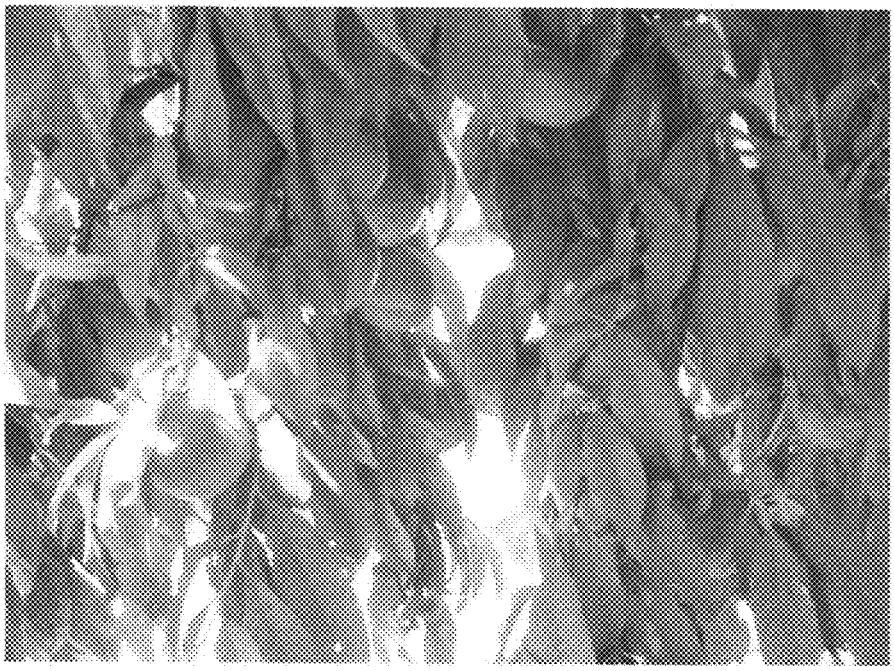
FIG. 3(*a*) and 3(*b*) are two photographs that show two enlarged views of typical specimens of the fruit and leaves on the tree of FIG. 2.
Figure 3B:
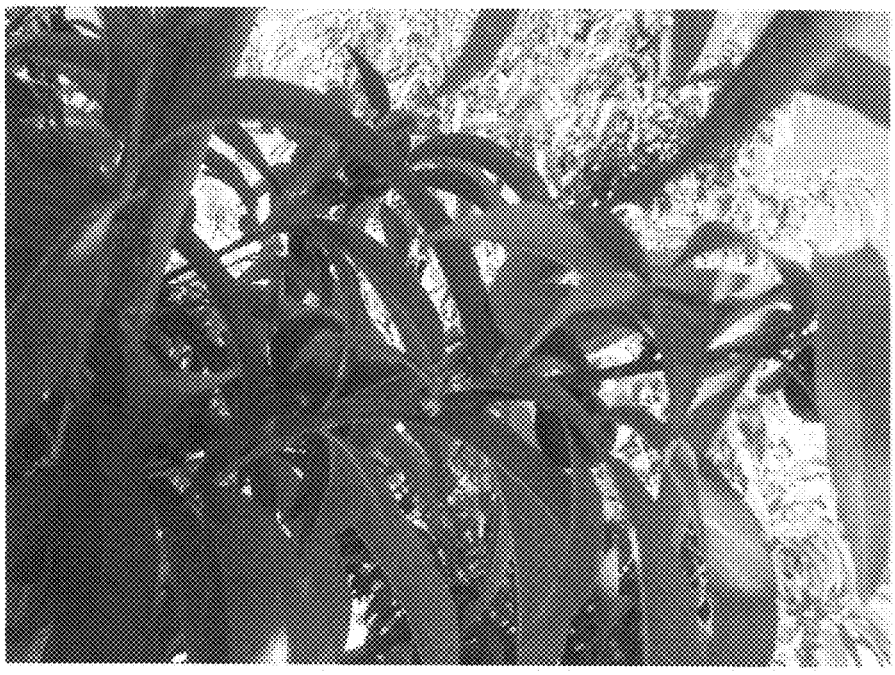

Characterization of 'Andes Nec-3' nectarine.

Tree:

1. *Size*.—Medium, similar to 'Bonanza'. An 8 year old tree is 4.3-4.5 m high shaped as an open vase, 2.5-3.0 of diameter.
2. *Vigor*.—Medium, similar to 'J.H. Hale'. Shoots reach 30 to 50 cm on regular spring/summer growing period.
3. *Habit*.—Horizontal, like 'Albertina'. It is well adapted to open vase training.

4. *Flowering shoot thickness* (*excluding brindilles*).—Medium, similar to 'Redhaven'. The typical and observed flowering shoot diameter is 0.4-0.6 mm.
5. *Flowering shoot length of internodes*.—Medium, similar to 'Redhaven'. The typical and observed flowering shoot internode length is 2.4-3.0 cm.
6. *Flowering shoot coloration*.—There is present anthocyanin coloration in the zone exposed to sunlight, reaching a light red color, that in coordinates a*, b* and L* of the CIELab space color (McGuire, 1992) corresponds to 45.21, 11.79, and 10.73, respectively, but in the lower part of the shoot the anthocyanin coloration is weak, similar to 'Springtime', reaching a light brown color, that in coordinates a*, b* and L* of the CIELab space color (McGuire, 1992) corresponds to 38.61, 8.14, and 11.01, respectively. (McGuire, R.G. 1992. Reporting of Objective Color Measurements. Hortscience. 27(12): 1254-1255).
7. *Flowering shoot density of flower buds*.—Medium, similar to 'Michelini', reaching in an average year 22-36 flowers/30 cm long shoot.
8. *Flowering shoot*.—General distribution of flower buds: In groups of two or more, similar to 'Redhaven'.
9. *The trunk of an* 8-*year old tree*.—Shows a 12-14 cm diameter, measured on 50 cm above the ground, the bark texture is smooth with few lenticels, and the bark color is dark brown, that in coordinates a*, b* and L* of the CIELab space color (McGuire, 1992) corresponds to 42.78, 3.33, and 11.33, respectively.
10. *The primary branches*.—Diameter reach 6-8 cm in an 8-year old tree, and the color is light brown, that in coordinates a*, b* and L* of the CIELab space color (McGuire, 1992) corresponds to 50.01, −2.02, and 22.49, respectively.
11. *Vegetative buds shape and color*.—Acuminate, 4.8-7.5 mm length, color brown that in coordinates a*, b* and L* of the CIELab space color (McGuire, 1992) corresponds to 97.04, −6.76, and 28.88, respectively.

Flower:

12. *Type*.—It has a showy type, similar to 'Robin', reaching a whole diameter of 2.6 to 3.0 cm, and ovary is settled 0.4 to 0.5 cm low the calyx Showy, similar to 'Robin'.
13. *Calyx color of inner side* (*opened flower, before falling of petals*).—Greenish yellow, similar to 'Robin', the color is classified as in coordinates a*, b* and L* of the CIELab space color (McGuire, 1992) corresponds to 62.01, 14, and 25.67, respectively.
14. *Corolla predominant color* (*inner side*).—Medium pink, similar to 'Fuzalode', classified in coordinates a*, b* and L* of the CIELab space color (McGuire, 1992) corresponds to 87.12, −1.21, and 10.13, respectively.
15. *Petal shape*.—Round, similar to 'Springtime'.
16. *Petal size*.—Medium, similar to 'Robin', 1.1 to 1.6 cm diameter.
17. *Petals number*.—Five, similar to 'Redhaven'.
18. *Stamens position compared to petals*.—Above 0.5 to 1.0 mm, similar to 'Redhaven'.
19. *Stamen number and length*.—There are 32-38 stam9ns per flower in average 1 cm, of white-cream color, in coordinates a*, b* and L* of the CIELab space color (McGuire, 1992) corresponds to 90.44, −4, and 10.11, respectively.
20. *Stigma position compared to anthers*.—Same level, similar to 'Crimson Gold'.
21. *Pistil*.—There is normally 1 per flower, 12 mm length and white cream color according to in coordinates a*, b* and L* of the CIELab space color (McGuire, 1992) corresponds to 62.94, 3.77, and 9.32, respectively.
22. *Anthers pollen*.—Present and abundant, similar to 'Redhaven', in number 32 to 39, and the characteristic color is classified in coordinates a*, b* and L* of the CIELab space color (McGuire, 1992) corresponds to 83.13, 4.21, and 43.43, respectively.
23. *Ovary shape*.—Pubescence is absent, similar to 'Fuzalode', green color classified as CIELA, and round shape.

Leaf:

24. *Leaf blade length*.—Long, reaching 13-15 cm long.
25. *Leaf blade width*.—Medium, reaching 4-5.5 cm width.
26. *Leaf blade*.—Ratio length/width: Medium, similar to 'Early Sungrand', reaching a ratio of 3.5.
27. *Leaf blade shape in cross section*.—Flat, similar to 'Mayred'.
28. *Leaf blade recurvature of apex*.—Absent, similar to 'Merril Sundance'.
29. *Leaf blade angle at base*.—Acute, less than 90°, similar to 'Springtime'.
30. *Leaf blade angle at apex*.—Medium to acute, similar to 'Earlyred'.
31. *Leaf blade color*.—Green, similar to 'Robin', classified in coordinates a*, b* and L* of the CIELab space color (McGuire, 1992) corresponds to 37.45, −8.18, and −15.51, respectively on the upper surface and in coordinates a*, b* and L* of the CIELab space color (McGuire, 1992) corresponds to 58.38, −5.73, and −12.7, respectively, in the lower surface.
32. *Petiole length*.—Short, similar to Redhaven', reaching 2-3 mm.
33. *Petiole*.—Two to four nectaries present, similar to 'Redhaven'.
34. *Petiole shape of nectaries*.—Reniform, similar to 'Redhaven'.
35. *Petiole predominant number of nectaries*.—More than two, similar to 'Everts'.

Fruit:

36. *Fruit size*.—Medium, similar to 'Sunhaven', ranging between 160 to 230 g.
37. *Fruit shape* (*in ventral view*).—Round, similar to 'Redwing'. The observed fruit length parallel to the suture is 5.5 to 6.7 cm and width perpendicular to the suture is 6.0 to 7.00 cm.
38. *Fruit shape of pistil end*.—Plane, similar to 'Redhaven'.
39. *Fruit symmetry* (*viewed from pistil end*).—Symmetric, similar to 'Morettini'.
40. *Fruit prominence of suture*.—Weak, similar to 'Redhaven'.
41. *Fruit depth of stalk cavity*.—Shallow, similar to 'Robin', ranging between 5-6 mm.
42. *Fruit width of stalk cavity*.—Medium, 1.8-2.0 cm.
43. *Fruit ground color*.—Greenish yellow, classified in coordinates a*, b* and L* of the CIELab space color (McGuire, 1992) corresponds to 62.09, 5.11, and 29.6, respectively, similar to 'Precoce de Hale' when is mature.

44. *Fruit over color*.—Present.
45. *Fruit*.—Hue of over color: Red, classified as CIELAB, similar to 'Red Diamond'.
46. *Fruit pattern of over color*.—Solid pattern, similar to 'Flavorcresf'.
47. *Fruit extent of over color*.—Large, reaching 98%.
48. *Fruit pubescence*.—Absent.
49. *Fruit thickness of skin*.—Medium, similar to 'Madame Girard'.
50. *Fruit adherence of skin to flesh*.—Strong, similar 'Babygold 5'.
51. *Fruit firmness of pulp*.—Firm, reaching 11.2 to 14 pounds when mature.
52. *Fruit ground color of flesh*.—Yellow, classified in coordinates a*, b* and L* of the CIELab space color (McGuire, 1992) corresponds to 63.74, 4.69, and 21.56, respectively.
53. *Fruit anthocyanin coloration directly under skin*.—Weakly expressed.
54. *Fruit anthocyanin coloration of flesh*.—Absent or very weakly expressed, similar to 'Robin'.
55. *Fruit anthocyanin coloration around stone*.—Absent or very weakly expressed, similar to 'Springtime'.
56. *Fruit texture of the flesh*.—Not fibrous, melting flesh type, similar to 'Redhaven'.
57. *Fruit sweetness*.—Medium to high, ranging 13.1 to 16.1.
58. *Fruit acidity*.—Medium, ranging between 1.0 to 1.3% malic acid when fruit is ripe.

Stone:

59. *Stone size compared to fruit*.—Medium, ranging between 8 to 12 g.
60. *Stone shape* (*in lateral view*).—Obovate, similar to 'Rubidoux'. The length is 2.8 cm and width 1.5 cm.
61. *Stone intensity of brown color*.—Medium, classified as in coordinates a*, b* and L* of the CIELab space color (McGuire, 1992) corresponds to 27.99, 16.11, and 7.56, respectively.
62. *Stone relief of surface*.—Pits similar to 'Madame Girard'.
63. *Stone grooves*.—Similar to 'Madame Girard'.
64. *Stone tendency of splitting* (*at peak harvest*).—Absent.
65. *Stone adherence to flesh*.—Present, similar to 'Sweet Gold'.
66. *Stone degree of adherence to flesh*.—Strong, similar to 'Vivian'.

Phenology:

67. *Time of leaf bud burst*.—Early, similar to 'Springtime'. On Southern Hemisphere is between 10th to 15th September.
68. *Time of beginning of flowering*.—Medium, similar to 'Redhaven'. On Southern Hemisphere is between 10th to 18th August.
69. *Duration of flowering*.—Short, 5-7 days.
70. *Time of maturity for consumption*.—Medium, similar to 'Fairhaven'. On Southern Hemisphere is between 21th to 28th January.
71. *Tendency to preharvest*.—Absent.
72. *Pest/disease resistance/susceptibility*.—This genotype is not genetically resistant to any common pest and disease of peach, as Mildew, leaf curl, bacterial canker, aphids, thrips or, Oriental moth.
73. *Fruit characterization*.—Is on table 1.

TABLE 1

Fruit characterization of nectarine 'Andes Nec-3'

| SEASON | Harvest Date | Blush (%) | Firmness (Lb) Equatorial Diameter | Shoulders | Suture | Tip | Soluble solids (°Brix) |
|---|---|---|---|---|---|---|---|
| 2009-2010 | 1/21 | 95 | 13.0 | 13.5 | 14.6 | 12.7 | 16.1 |
| 2010-2011 | 1/28 | 100 | 12.0 | 12.4 | 13.3 | 14.7 | 15.2 |
| 2011-2012 | 1/23 | 100 | 11.8 | 13.0 | 13.2 | 12.9 | 13.1 |

GENERAL TECHNICAL NOTES

Very good outward appearance. Excellent color coverage. Fruit round, no tip. High productivity. Good flavor.

CONCLUSIONS

After five years of evaluation, the variety continues to show its outstanding characteristics: very good productivity, good size, good flavor and good external appearance. High potential for export purposes because of exceptional post-harvest life.

Having thus described and illustrated the new variety of nectarine tree, I claim:

1. A new and distinct variety of nectarine tree, substantially as illustrated and described, that is similar to 'Flavortop' nectarine by producing nectarines that are yellow in flesh color, firm in texture, and balanced acid/sweet flavor, but is distinguished therefrom by having a more extend red blush, by its better taste, and longer postharvest life potential, and by producing fruit that is clingstone instead of freestone.

* * * * *